United States Patent [19]

Yamamoto et al.

[11] 4,371,686
[45] Feb. 1, 1983

[54] ANTITHROMBOGENIC, HIGHLY ELASTIC POLYURETHANE COMPOUND

[75] Inventors: Noboru Yamamoto, Ikeda; Iwao Yamashita, Kawanishi, both of Japan

[73] Assignee: Agency of Industrial Science & Technology Ministry of International Trade & Industry, Tokyo, Japan

[21] Appl. No.: 302,119

[22] Filed: Sep. 14, 1981

[30] Foreign Application Priority Data

Sep. 12, 1980 [JP] Japan ............................. 55-127837

[51] Int. Cl.³ ...................... C08G 18/32; C08G 18/48
[52] U.S. Cl. ...................................... 528/76; 528/61; 528/62; 528/64; 528/904
[58] Field of Search ................. 521/905, 914; 528/61, 528/62, 904, 76, 64

[56] References Cited

U.S. PATENT DOCUMENTS

| | | | |
|---|---|---|---|
| 2,929,804 | 3/1960 | Steuber | 528/64 |
| 3,071,557 | 1/1963 | Frazer et al. | 528/64 |
| 4,131,604 | 12/1978 | Szycher | 528/76 |
| 4,182,827 | 1/1980 | Jones et al. | 521/905 |
| 4,243,760 | 1/1981 | McDaniel et al. | 521/176 |
| 4,301,110 | 11/1981 | Cuscurida et al. | 521/914 |

OTHER PUBLICATIONS

K. Furusawa et al., Kobunshi Ronbunshu No. 34, p. 309 (1977).
C. T. Chen et al, Journ. of Applied Polymer Sci. vol. 16 pp. 2105-2114 (1972) "Synthesis, Characterization, and Permeation Properties of Polyether-Based Polyurethanes".
E. Nyilas, J. Biomed. Mater. Res. Symposium, No. 3, pp. 129-154 "Development of Blood-Compatible Elastomers. II Hematologic (1972) Effects of Avcothane Intra-Aortic Balloon Pumps in Cardiac Patients".
B. Jansen et al. Journ. of Polymer Sci. Symp. 66, pp. 465-473 ('79) "Radiation-Induced Modification of Polyurethane-Elastomers with Hydroxyethyl Methacrylate".
S. D. Bruck, J. Biomed. Mater. Res. Symp. No. 8, pp, 1-21 (1977) "Interactions of Synthetic and Natural Surfaces with Blood in the Physiological Environment".
J. W. Boretos et al. J. Biomed. Mater. Res., vol. 9, pp. 327-340 "Surface and Bulk Characteristics of a Polyether (1975) Urethane for Artifical Hearts".
J. W. Boretos et al. J. Biomed. Mater. Res., vol. 2, pp. 121-130 (1968) "Segmented Polyurethane: A Polyether Polymer".
E. Nyilas, J. Biomed. Mater. Res. Symposium, No. 3, pp. 97-127 "Development of Blood Compatible Elastomers. II Performance (1972) of Avcothane Blood Contact Surfaces in Exper. Animal Implantations.

Primary Examiner—H.S. Cockeram
Attorney, Agent, or Firm—Oblon, Fisher, Spivak, McClelland & Maier

[57] ABSTRACT

An antithrombogenic, highly elastic polyurethane compound produced by the reaction of a polyether diol with a diisocyanate and a diamine, which polyurethane compound is characterized by said polyether diol being a compound of the general formula:

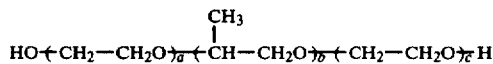

wherein, a, b, and c each denote a positive integer and having a polyoxyethlene content in the range of from 10 to 50 weight percent and an average molecular weight in the range of from 500 to 5,000.

9 Claims, No Drawings

ANTITHROMBOGENIC, HIGHLY ELASTIC POLYURETHANE COMPOUND

BACKGROUND OF THE INVENTION

This invention relates to an antithrombogenic, highly elastic polyurethane compound suitable for biomedical materials. More particularly, this invention relates to an antithrombogenic, highly elastic polyurethane compound excellent in biocompatibility and mechanical properties, which is produced by the reaction of a diisocyanate and a diamine upon a polyoxyethylene-polyoxypropylene-block copolyether having hydroxyl terminal groups.

The biomedical materials, particularly those for use in devices exposed to contact with blood such as, for example, catheters, A-V shunts for artificial kidneys, artificial lungs, blood bypass tubes, pumping chambers for artificial hearts, and balloon pumping materials, are required to possess blood compatibility and biocompatibility and mechanical properties such as flexibility, elasticity, durability, and wet toughness.

Generally, synthetic polymers stable under physiological environment are conveniently used as elastic biomedical materials. Unfortunately, silicone and plasticized polyvinyl chloride, which have the above-mentioned properties, are insufficient in antithrombogenicity. This fact constitutes itself a serious drawback for biomedical materials which are to be used at positions exposed to contact with blood. To overcome the drawback, there have been developed various devices aimed at vesting these synthetic polymeric compounds with an antithrombogenicity.

It has been known to impart an antithrombogenicity to polymers by blending an anticoagulant such as heparin or urokinase into such compounds or chemically combining such compounds with the anticoagulant. This impartment of the antithrombogenicity, however, is accomplished at the expense of mechanical properties. The antithrombogenicity thus imparted has a disadvantage that it is wholly or partially lost when the compounds are subjected to a treatment for thermal sterilization.

Certain polyurethane compounds have been demonstrated to possess an antithrombogenicity. Some of them have already been commercialized. They are represented by the following general formula.

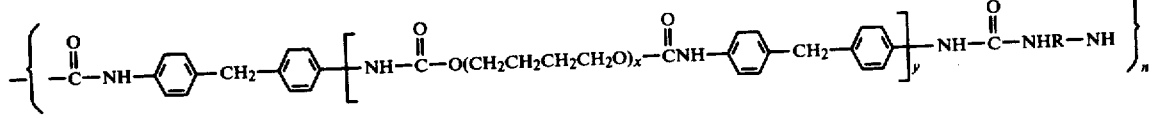

(wherein, R denotes an aromatic group). Although they excel in strength and elasticity, their hydrophilicity and antithrombogenicity are not quite satisfactory. [Literature: J. W. Boretos et al., J. Biomed. Mater. Res., 2, 121 (1968), 9, 327(1975)]

A blockcopolymer of a polyurethane compound and silicone resin has also been demonstrated to possess an antithrombogenicity. [Product marketed under trademark designation of Avcothane, Literature: E. Nylas et al., J. Biomed. Mater. Res. Symp., 3, 97, 129(1972)]

This copolymer has a disadvantage that it can be produced only by a highly complicated process, is readily torn, and tends to adsorb lipids.

A polyurethane compound having a polyoxyethylene block as a soft segment has been reported. [Literature: C. T. Chen et al., J. Appl. Polm. Sci., 16, 2105(1972), Kiyotaka Furusawa et al., Kobunshi Ronbunshu, 34, 309(1977)]. Although this compound manifests an antithrombogenicity, it exhibits elasticity and other mechanical properties at very low levels and readily undergoes hydrolysis. Thus, it finds little practical utility.

A product obtained by grafting a hydroxyl-containing compound to a polyurethane compound has been demonstrated to possess an antithrombogenicity. It has unsatisfactory mechanical strength for practical use. [Literature: S. D. Bruck, J. Biomed. Mater. Res. Symp., 8, 1 (1977), B. Jansen et al., J. Polym. Sci., Symp. 66, 465(1979)].

All the efforts made to date have yielded results which suggest that the incorporation of hydrophilic groups to improve various polyurethane compounds in their antithrombogenicity result in the decrease of their mechanical properties. Thus, it is thought difficult to obtain compounds suitable for practical use.

An object of this invention is to provide a novel polyurethane compound which retains intact the antithrombogenicity possessed inherently by polyurethane compounds or exhibits this property to an enhanced extent, excels in elasticity, resistance to hydrolysis, wet toughness and other mechanical properties, and excellent biocompatibility.

SUMMARY OF THE INVENTION

To accomplish the object described above according to the present invention, there is provided a polyetherpolyurethane compound which is obtained by the reaction of a diamine type compound upon a prepolymer resulting from the reaction of a diisocyanate upon a specific polyoxyethylene-polyoxypropylene-copolyether diol. More specifically, this invention provides an antithrombogenic, highly elastic polyurethane compound which is obtained by the reaction of a diisocyanate and a diamine upon a polyether diol represented by the general formula:

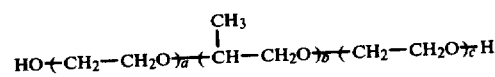

(wherein, a, b, and c each denote a positive integer) and containing 10 to 50 weight percent of polyoxyethylene and having an average molecular weight in the range of from 500 to 5,000.

DESCRIPTION OF THE PREFERRED EMBODIMENT

The polyurethane compound of this invention contains in the main chain thereof, as a soft segment, a block copolyether represented by the general formula:

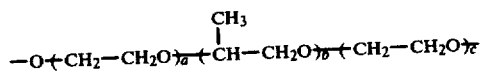

(wherein, a, b, and c each denote a positive integer) and containing 10 to 50 weight percent of polyoxyethylene and having an average molecular weight in the range of from 500 to 5,000. When the polyoxyethylene content is less than 10 weight percent, the polyurethane compound does not possess sufficient antithrombogenicity. When the polyoxyethylene content exceeds 50 weight percent, the polyurethane compound proves undesirable because it exhibits elasticity, flexibility, and wet strength at intolerably low levels. When the average molecular weight is less than 500, the polyurethane compounds are deficient in various properties in general such as antithrombogenicity and mechanical properties. When the average molecular weight exceeds 5,000, the polyurethane compound has a disadvantage that it exhibits insufficient strength and poor workability. For use in biomedical materials intended for prolonged exposure to blood, the polyurethane compound is desired to have a polyoxyethylene content in the range of from 10 to 40 weight percent and an average molecular weight in the range of from 1,000 to 3,000.

The novel polyurethane compound of this invention can be produced by the same method as that used for the synthesis of ordinary polyurethane compounds.

To be specific, a polyether diol represented by the general formula:

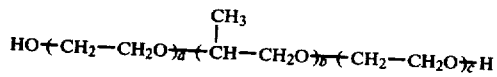

(wherein, a, b, and c each denote a positive integer) having a polyoxyethylene content of from 10 to 50 weight percent and an average molecular weight in the range of from 50 to 5,000 is caused to react with a diisocyanate in an organic solvent such as dimethyl sulfoxide or dimethyl acetamide which is widely used in the production of urethane resins at a temperature in the range of from 50° to 100° C., to produce a prepolymer.

The polyether diol mentioned above is commercially available as a surfactant or emulsifier.

The diisocyanate is not specifically limited. Any of the known diisocyanate compounds used for the synthesis of urethane resins can be adopted. Examples of diisocyanates which are usable advantageously in this invention include aromatic diisocyanates such as diphenylmethane diisocyanate, 2,4-(or 2,6-)-tolylene diisocyanate, p-xylylene diisocyanate, and 1,5-naphthylene diisocyanate, alicyclic diisocyanates such as methylcyclohexane diisocyanate and 4,4'-dicyclohexylmethane diisocyanate, and aliphatic diisocyanates such as hexamethylene diisocyanate.

Preferably, this reaction is carried out in the absence of a catalyst.

Then, a diamine type compound is added in the neighborhood of room temperature to the reaction solution containing the aforementioned prepolymer and the added diamine type compound is caused to react with the prepolymer in conjunction with the aforementioned diisocyanate. Consequently, the polyurethane compound of the present invention is obtained.

The diamine type compound to be used in this case is not specifically limited. Any of the diamine type compounds which are generally used for the synthesis of polyurethane resins can be used. Examples of diamine type compounds which are particularly advantageously used in this invention include hydrazine, aliphatic diamines such as ethylene diamine and hexamethylene diamine, aromatic diamines such as p-xylene diamine, 2,4-tolylene diamine, and p-diphenylmethane diamine, and aromatic dihydrazides such as dihydrazide terephthalate and dihydrazide isophthalate.

In the preparation of the prepolymer, the diisocyanate is used in the amount of 1.5 to 4 mols, preferably about 2 mols, based on 1 mol of the polyether diol. The amount of the diamine to be added to the prepolymer is in the range of from 0.5 to 3 mols, preferably about 1 mol, per mol of the polyether diol.

The polyurethane compound of this invention is excellent in antithrombogenicity, biocompatibility, flexibility, elasticity, durability, resistance to hydrolysis, and wet toughness and, therefore, is suitable for as a biomedical material, particularly as a material for use in devices exposed to contact with blood. The polyurethane compound of this invention can be used in various ways. For example, it can itself be molded into various medical devices, can be dissolved in a solvent such as dimethyl formamide or dimethyl acetamide and used to coat such devices, or can be formed into sheets or films.

Now, the present invention will be described more specifically below with reference to working examples.

Examples 1-3 and Comparative Experiments 1-6:

In 200 ml of dimethyl sulfoxide, 20 g (0.02 mol) of an A-B-A type copolyether diol (PEO-PPO) consisting of polyoxyethylene (A) blocks and polyoxypropylene (B) block, containing 10 weight percent of A blocks, having an average molecular weight of 1100, and possessing hydroxyl terminal groups and 10 g (0.04 mol) of diphenylmethane diisocyanate were uniformly dissolved. Under introduction of nitrogen gas, the resultant solution was stirred at 80° C. for five hours. Subsequently, the reaction solution was cooled to room temperature. To the solution, 150 ml of dimethyl formamide containing 1.2 g (0.02 mol) of ethylene diamine was added dropwise (without the separation of a prepolymer). The resultant mixture was stirred for 24 hours. The resultant reaction solution was poured in water to precipitate the formed polyurethane compound. The polyurethane compound was separated by filtration, then treated with ethanol in a Soxlet extractor to remove low-molecular compounds. The residue was vacuum dried at room temperature to afford the polyurethane compound. The intrinsic viscosity of this compound, determined by using dimethyl formamide as the solvent, was found to be 0.7 dl/g.

Then, a 15-percent dimethyl formamide solution of the polyurethane compound obtained as described was poured in a flat dish. Under a vacuum, the solution was subjected to gradual evaporation to expel the solvent. Consequently, there was obtained a uniform film.

This film was tested for tensile properties. For evaluation of water absorbing property, the film was immersed in water at 37° C. for 24 hours, and water drops on the film were blotted with filter paper. By measuring the change of weight before and after the immersion in water, the water content of the film was determined. With a tensile tester (Toyo Baldwin Co.), it was tested for strength at break, elongation at break, and 100% modulus at 20° C. The results were as shown in Table 1.

For a fatigue test, the film was exposed to tension enough to produce 30 percent elongation and, as kept under this tension, was immersed in water at 37° C. for three days. At the end of this period, the film was removed from water and tested for possible change in strength at break and elongation at break. This test showed no discernible degradation in strength, elongation and modulus of elasticity. From the test results, it is seen that the polyurethane compound of this invention possesses such strength, elasticity, durability, resistance to hydrolysis, and wet strength as are required of biomedical materials.

Subsequently, the polyurethane compound was tested for antithrombogenicity. The evaluation of the antithrombogenicity was carried out by the Lee-White method and the Imai method. To be specific, 1 ml of a 5- percent tetrahydrofuran-dimethyl acetamide (volume ratio 1:1) solution of the polyurethane compound obtained as described above was measured out and placed in a test tube with a ground top and stopper 12 mm in diameter and 10 cm length. The test tube was connected to a rotary evaporator and rotated under a vacuum, to have the solution uniformly applied in the form of a coat to the inner wall of the test tube. Then, 1 ml of fresh human blood was placed in the test tube and held at 37° C. After the elapse of five minutes, the test tube was tilted 45° at intervals of 30 seconds to examine the coagulation of the blood. The length of time which elapsed until the blood inside the test tube ceased to show any sign of flow was noted as the coagulation time (Lee-White method).

Separately, the polyurethane compound of this invention was molded in the shape of a film 50 microns in thickness. This film was immersed in distilled water for two to three days. During this period, the distilled water was replaced four times. A 3-cm square of the film thus treated was placed fast on the depressed side of a watch glass with a ground lid. At the constant temperature of 37° C., 0.25 cc of ACD blood from a dog was superposed on the film and 0.025 cc of a 0.1 M aqueous calcium chloride solution was added to the blood to initiate blood coagulation. After the elapse of 10 or 13 minutes, the reaction of blood coagulation was stopped by addition of water. The blood clot thus formed was fixed with formalin, air dried at room temperature overnight and then weighed. A blank test was conducted by repeating the procedure on the watch glass now empty of the film. The relative weight of the blood clot obtained on the film to the weight of the blood clot obtained in the blank test taken as 100 was used as the degree of antithrombogenicity of the film (Imai method).

The coagulation time and the relative weight thus obtained were as shown in Table 2. The same evaluation was repeated on the films of polyurethane compounds obtained by following the procedure of Example 1, except that there were used polyoxyethylene-polyoxypropylene-copolyether diols having an average molecular weight of 2,000 and polyoxyethylene contents of 10 weight percent (2) and 40 weight percent (3). For the purpose of comparison, the same evaluation was conducted on the films of polyurethane compounds prepared by following the procedure of Example 1, except that polyoxypropylene glycols (PPO) having average molecular weights of 1,000 and 2,000, a mixture of polyoxypropylene glycol (PPO) having an average molecular weight of 2,000 and polyoxyethylene glycol (PEO) having an average molecular weight of 600 (PPO/PEO=9/1), and polyoxytetramethylene glycol (PTMO) having an average molecular weight of 2,000 were used each as a polyether component and the reaction temperature was fixed at 110° C. The evaluation was further carried out on the film of a commercially available polyurethane of medical grade Biomer (made by Ethycon Corp.). The results were as shown in Table 1 and Table 2.

TABLE 1

| Sample Kind (polyether component) | Average molecular weight | PEO content (%) | Water content (%) | Tensile strength at break (kg//cm$^2$) | 100% modulus of elasticity (kg$^f$/cm$^2$) | Elongation at break (%) |
|---|---|---|---|---|---|---|
| Example | | | | | | |
| 1 PPO — PEO | 1100 | 10 | 0.4 | 210 | 75 | 1100 |
| 2 PPO — PEO | 2000 | " | 3.2 | 190 | 44 | 1400 |
| 3 PPO — PEO | " | 40 | 9.1 | 120 | 28 | 1800 |
| Comparative Example | | | | | | |
| 1 PPO | 1000 | — | — | 170 | 59 | 680 |
| 2 PPO | 2000 | — | — | 120 | 33 | 150 |
| 3 PPO + PEO | — | — | — | 40 | 22 | 670 |
| 4 Biomer | — | — | — | 430 | 27 | 1000 |
| 5 PTMO | 2000 | — | 0.1 | 340 | 35 | 800 |

TABLE 2

| Sample Kind (polyether component) | Average molecular weight | PEO content (%) | Coagulation time (min.) | Relative weight of clot (%) 10 min. | Relative weight of clot (%) 13 min. |
|---|---|---|---|---|---|
| Example | | | | | |
| 1 PPO — PEO | 1100 | 10 | 27 | — | — |
| 2 PPO — PEO | 2000 | " | 30 | 26 | 60 |
| 3 PPO — PEO | " | 20 | 29 | 55 | 71 |
| Comparative Example | | | | | |
| 1 PPO | 1000 | — | 20 | — | — |
| 2 PPO | 2000 | — | — | 93 | 7100 |
| 4 Biomer | — | — | 21 | 79 | — |
| 5 PTMO | 2000 | — | — | 54 | 87 |
| 6 (Watch glass) | — | — | 11 | 100 | 100 |

It is seen from Table 2 that the polyurethane compounds of the present invention exhibit excellent antithrombogenicity.

Comparative Experiment 7

A polyurethane compound was prepared by following the procedure of Example 1, except that polyoxyethylene glycol having an average molecular weight of 1000 was used as a polyether component. It was tested for mechanical strength, water absorbing property, and antithrombogenicity. The results were as shown below.

TABLE 3

| Water content (%) | Tensile strength (kg$^f$/cm$^2$) | 100% modulus of elasticity (kg$^f$/cm$^2$) | Elongation at rupture (%) | Coagulation time (min.) | Relative weight of clot (%) 10 min. | Relative weight of clot (%) 13 min. |
|---|---|---|---|---|---|---|
| 95 | 88 | 30 | 950 | 36 | 22 | 45 |

Although this polyurethane compound showed nearly the same degree of antithrombogenicity as the polyurethane compounds of this invention, it showed notably low strength at break. Because of its unusually high water absorbing property and susceptibility to hydrolysis, its strength in water was hardly enough for practical use.

Example 4

Glass rods 3 to 5 mm in diameter and 10 cm in length were immersed in a 15 weight percent dimethyl formamide solution of the same polyurethane compound as prepared by the procedure of Example 1. They were taken out and dried at 60° C. to form a coat of the polyurethane compound on the glass rods. This procedure was repeated until the coat gained sufficient thickness. The coated glass rods were then immersed in ethanol to separate the coats from the glass rods. Thus, tubes of polyurethane compound having varying thicknesses were obtained.

Of the tubes thus obtained, those having a wall thickness of 0.5 mm, an inside diameter of 4 mm, and a length of 2 cm were implanted in the jugular veins and the femoral veins of dogs. After the elapse of two hours, and 24 hours, the tubes were removed from the veins and examined for deposition of blood clot. No blood clot was found on any of the tubes.

What is claimed is:

1. An antithrombogenic, highly elastic, uncrosslinked polyurethane compound produced by the reaction of a polyether diol of the general formula:

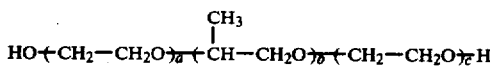

wherein, a, b, and c each denote a positive integer, having a polyoxyethylene content in the range of from 10 to 50 weight percent and an average molecular weight in the range of from 500 to 5,000, with 1.5 to 4 mols of a diisocyanate per mol of said polyether diol to give a prepolymer followed by reacting said prepolymer with 0.5 to 3 mols of a diamine per mol of said polyether diol to give said uncrosslinked polyurethane.

2. The antithrombogenic polyurethane compound according to claim 1, wherein said polyether diol has a polyoxyethylene content in the range of from 10 to 40 weight percent and an average molecular weight in the range of from 1,000 to 3,000.

3. The antithrombogenic polyurethane compound according to claim 1, wherein said compound has a tensile strength at break of at least 120 kg/cm².

4. The antithrombogenic polyurethane compound according to claim 1, wherein said compound has a 100% modulus of elasticity of at least 28 kg/cm².

5. The antithrombogenic polyurethane compound according to claim 1, wherein said compound has an elongation at break of at least 1100%.

6. A method for the manufacture of an antithrombogenic device exposed to contact with blood, which comprises molding an antithrombogenic, highly elastic, uncrosslinked polyurethane compound produced by the reaction of a polyether diol of the general formula:

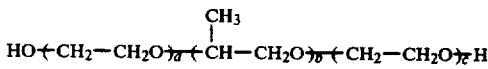

wherein, a, b, and c each denote a positive integer, having a polyoxyethylene content in the range of from 10 to 50 weight percent and an average molecular weight in the range of from 500 to 5,000, with 1.5 to 4 mols of a diisocyanate per mol of said polyether diol to give a prepolymer followed by reacting said prepolymer with 0.5 to 3 mols of a diamine per mol of said polyether diol to give said uncrosslinked polyurethane.

7. The method according to claim 6, wherein said polyether diol contains 10 to 30 weight percent of polyoxyethylene and has an average molecular weight in the range of from 1,000 to 3,000.

8. A method for the manufacture of an antithrombogenic film to be deposited as a coating on the surface of a device, which comprises dissolving in a solvent an antithrombogenic, highly elastic, uncrosslinked polyurethane compound produced by the reaction of a polyether diol of the general formula:

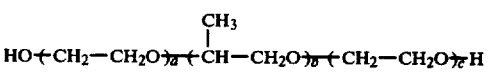

wherein, a, b, and c each denote a positive integer, having a polyoxyethylene content in the range of from 10 to 50 weight percent and an average molecular weight in the range of from 500 to 5,000, with 1.5 to 4 mols of a diisocyanate per mol of said polyether diol to give a prepolymer followed by reacting said prepolymer with 0.5 to 3 mols of a diamine per mol of said polyether diol to give uncrosslinked polyurethane, and applying the resultant solution to the surface of a device.

9. The method according to claim 8, wherein said polyether diol contains 10 to 30 weight percent of polyoxyethylene and has an average molecular weight in the range of from 1,000 to 3,000.

* * * * *